(12) United States Patent
Brinkerhoff et al.

(10) Patent No.: US 7,451,507 B2
(45) Date of Patent: Nov. 18, 2008

(54) COMPRESSION HEAD PILLOWS AND NECK ANGLE ADJUSTMENT MECHANISM FOR REFRACTIVE LASER SURGERY AND THE LIKE

(75) Inventors: Mark Brinkerhoff, San Jose, CA (US); Tom Kowalski, Ben Lomand, CA (US); Shandon Alderson, San Jose, CA (US)

(73) Assignee: AMO Manufacturing USA, LLC, Milpitas, CA (US)

( * ) Notice: Subject to any disclaimer, the term of this patent is extended or adjusted under 35 U.S.C. 154(b) by 340 days.

(21) Appl. No.: 11/335,177

(22) Filed: Jan. 18, 2006

(65) Prior Publication Data
US 2007/0163049 A1   Jul. 19, 2007

(51) Int. Cl.
*A47C 20/00* (2006.01)
(52) U.S. Cl. .......................................... 5/637
(58) Field of Classification Search ................ 5/622, 5/637, 640, 636, 613, 617
See application file for complete search history.

(56) References Cited

U.S. PATENT DOCUMENTS

| | | | |
|---|---|---|---|
| 3,226,106 A * | 12/1965 | Johnson et al. ................ 5/613 |
| 3,554,599 A | 1/1971 | Pietschmann | |
| 4,321,718 A | 3/1982 | Chern | |
| 4,447,922 A | 5/1984 | Brochu | |
| 4,700,691 A | 10/1987 | Tari | |
| 4,885,918 A * | 12/1989 | Vaccaro ........................ 600/22 |
| 5,090,073 A | 2/1992 | Nordan | |
| 5,144,630 A | 9/1992 | Lin | |
| 5,305,754 A * | 4/1994 | Honeywell et al. ............. 5/626 |
| 5,556,169 A | 9/1996 | Parrish | |
| 5,742,626 A | 4/1998 | Mead | |
| 6,460,207 B1 * | 10/2002 | Papay et al. .................... 5/640 |
| 6,594,839 B1 | 7/2003 | Papay | |
| 2003/0004500 A1 | 1/2003 | Clapham | |
| 2003/0009159 A1 | 1/2003 | Clapham | |
| 2004/0049852 A1 | 3/2004 | Phillips | |
| 2005/0066444 A1 | 3/2005 | Mazzei | |

* cited by examiner

*Primary Examiner*—Patricia Engle
*Assistant Examiner*—William Kelleher

(57) ABSTRACT

Improved devices, systems, and methods support and/or restrain a head of a patient, optionally for use in refractive surgery. Both the height of the patient's head and the angle of the patient's neck along the medial-lateral plane of the patient can be established independently, and compression pillow systems can gently and atraumatically compress the patient's head between protruding foam sidewalls or the like to inhibit movement of the patient from the alignment position.

7 Claims, 12 Drawing Sheets

COMPRESSION HEAD PILLOWS AND NECK ANGLE ADJUSTMENT MECHANISM FOR REFRACTIVE LASER SURGERY AND THE LIKE

BACKGROUND OF THE INVENTION

The present invention relates generally to devices, systems, and methods for supporting, positioning, and maintaining positions of a patients, often for performing refractive surgery on the eyes and the like. Embodiments of the invention provide an improved head support pillow which engages the sides and/or back of a head of the patient so as to position and/or restrain the head. Other embodiments provide mechanisms for vertically positioning the head and neck of a patient independently, facilitating positioning of the head at a desired or comfortable angle. The invention may be particularly useful for enhancing the speed, ease, safety, and efficacy of laser eye surgical procedures such as photorefractive keratectomy ("PRK"), laser in situ keratomileusis ("LASIK"), and the like.

Laser eye surgical procedures typically employ ultraviolet or infrared lasers to remove a microscopic layer of stromal tissue from the cornea to alter the cornea's refractive properties. Excimer laser systems generally use argon and fluoride gas to create a non-thermal laser light which can break molecular bonds in a process known as photoablation. Such systems result in the photodecomposition of the corneal tissue, but generally do not cause significant thermal damage to adjacent and underlying tissues of the eye. The photoablation removes the stromal tissue to change the shape or contour of the cornea, and can be used to correct myopia (near-sightedness), hyperopia (farsightedness), astigmatism, high-order aberrations, and the like.

Accurate photoablation of corneal tissue benefits from precise and stable alignment between the eye and the therapeutic laser beam transmitted from the laser system. Many laser eye surgical alignment systems have a patient seat or bed so that the patient is treated while seated, while lying down, or while reclined in a supine position. To align the patient with the laser beam delivery optics, the system operator often moves the seat or bed into alignment with the laser system. A particularly advantageous user interface and patient support system is described in U.S. patent application Ser. No. 10/226,867, entitled "Improved Interface for Laser Eye Surgery" as filed on Aug. 20, 2002, the full disclosure of which is incorporated herein by reference. Embodiments of that advantageous system make use of a contoured patient treatment chair to help position a patient into nominal alignment with the laser, allowing the system operator to make fine adjustments. As the system can be moved quickly to the nominal alignment for treatment of the left or right eyes, this improved interface system provides significant advantages in ease of use, overall procedure speed, and alignment accuracy.

While known patient support and user interface systems have allowed a large number of patients to benefit from the advantages of laser eye surgery, still further improvements would be desirable. For example, it would be advantageous to more flexibly and accurately position the patient, and to inhibit movement of the patient from the aligned configuration. It would also be advantageous to comfortably accommodate a wide range of patient physiologies, ideally without decreasing the speed or increasing the complexity of the alignment procedure. Preferably, these benefits would be provided without decreasing the system operator's access to the patient. At least some of these potential advantages may be realized by the systems, devices, and methods described hereinbelow.

BRIEF SUMMARY OF THE INVENTION

The present invention generally provides improved devices, systems, and methods for supporting, positioning, and/or maintaining a position of a patient. In exemplary embodiments, the techniques described herein will be particularly well suited for use in refractive surgery, for example by helping to position a patient relative to a therapeutic laser beam, inhibiting motion of the patient during a procedure, and the like. Exemplary embodiments may allow both the height of the patient's head and the angle of the patient's neck (particularly along the medial-lateral plane of the patient) to be established independently. This can help in orienting the patient's optical axis in alignment with a treatment axis of the laser beam, avoiding any need for the patient to be looking upward or downward and limiting the desired displacement of the patient's upper and lower eyelids during treatment. Other embodiments include novel compression pillow systems and methods which gently and atraumatically compress the patient's head between protruding foam sidewalls or the like to increase stability and inhibit movement of the patient from the alignment position.

In a first aspect, the invention provides a positioning mechanism for supporting a patient during refractive surgery. The patient has a head, a neck, and a body. The positioning mechanism comprises a patient support for supporting the body of the patient. The patient support has a head positioning base. A head pad is provided for engaging the head of the patient, and a neck pad is provided for engaging the patient adjacent the neck of the patient. A first linkage movably supports the head pad relative to the base, with articulation of the first linkage translating the head pad so as to vary a height of the head. A second linkage movably supports the neck pad relative to the base. Articulation of the second linkage translates the neck pad so as to vary an angle of the head. The articulation of the second linkage and movement of the neck pad will often be independent of articulation of the first linkage and movement of the head pad.

Advantageously, varying the vertical position of the head pad and the neck pad can allow the system operator to vary both patient head height and angle, with angularity adjustment achieved by increasing or decreasing the relative vertical positions of the head and neck pads. While some embodiments may be driven, optionally via remote control using an electric motor, hydraulic motor, or the like, many embodiments may be manually powered. Driven and/or manual embodiments may have a brake (for example, an electric brake) to enhance stability.

In exemplary embodiments, each linkage linearly translates its associated pad, often limiting the pad to this linear movement relative to the base. For example, the first and/or second linkage may comprise a scissor linkage. Such scissor linkages may include a stationary body coupled to a moving body by a threaded rod such that rotation of the threaded rod moves the moving body relative to the stationary body. This movement changes an angle between a plurality of scissor link pairs. The scissor links of each scissor link pair are coupled together by a pivotal joint, often disposed near the center of each scissor link. One of the scissor link pairs includes a first scissor link pivotally coupled to the stationary body and a second scissor link pivotally coupled to the moving body. Each linkage may also include a linkage top, with a pivotal joint and a sliding joint coupling the linkage top to the scissor link pairs so that the linkage top remains aligned with the base as the linkage top moves linearly during articulation of the scissor linkage.

Each linkage may include an associated input which is accessible by a system operator from adjacent the head of the patient. Actuation of the input may independently articulate the associated linkage so as to independently vary a height of its associated pad. One or both input may comprise a handle including a releasable lock having a height adjustment mode and an adjustment inhibiting mode, with the locking mechanism preferably switching modes in response to a movement of the handle. An exemplary input system includes such a locking handle for the head pad, with both inputs comprising handles in the form of rotatable knobs. The patient support can generally define a caudal and cranial orientation relative to the patient (for example, upward and downward relative to the patient), with rotatable handles preferably extending cranially (or upward relative to the patient) from the linkages so as to mechanically articulate the linkages when the handles are rotated.

The head of the patient may define a medial-lateral plane, with actuation of the positioning mechanism varying the angle of the head only along the medial-lateral plane. For example, raising and lowering the head pad may predominately lift the head vertically, while raising and lowering of the neck pad may primarily change the angle of the head upward or downward relative to the patient's face, raising and lowering the patient's chin.

In another aspect, the invention provides a method for positioning a patient for refractive surgery. The method comprises supporting the patient on a support so that the head of the patient is supported by a head pad, and so that a neck pad engages the patient adjacent a neck of the patient. A first linkage is articulated so as to vary a height of the head pad, and a second linkage is articulated independently of the first linkage so as to vary a height of the neck pad and the angle of the head.

Articulating of each linkage may generally comprise linearly translating its associated pad, with the linkages optionally inhibiting rotation of the pads, eccentric lateral (relative to the patient) movement of the pad, and the like.

In another aspect, the invention provides a head restraint mechanism for restrainingly supporting a head of a patient. The head restraint mechanism comprises a head pad body having a left sidewall and a right sidewall extending from a central region therebetween. The head pad is configured to receive the head of the patient between the left and right sidewalls when the back of the head is adjacent the central region. A linkage is coupled to the head pad body, with actuation of the linkage articulating the head pad body so as to move the left and right sidewalls inward, and to laterally compress the head therebetween sufficiently to inhibit movement of the head.

Preferably, the head pad body comprises a deformable foam, often comprising a urethane foam, a pressure sensitive visco-elastic foam, or the like, and will laterally compress the head so as to comfortably inhibit movement of the head. The sidewalls may have ear recesses, and a variety of linkages may be used to articulate the head pad body, with the central region often acting at least in part as a living hinge. Exemplary linkages may move a middle portion of the central region downward and/or move laterally offset portions of the central region (adjacent the sidewalls) upward so as to apply a gentle compressive force between the sidewalls and the sides of the patient's head.

An exemplary linkage for articulating the head pad body comprises vertically translatable cam. The cam can be moved vertically by the axial motion of a leadscrew driven cam follower. The cam is connected to the central portion of the pillow such that its vertical motion moves the pillow center downward or upward. Since the pillow can be pivotally supported beneath the right and left sides of the patient's head, downward motion of the pillow center can draw both sidewalls of the pillow inward to gently compress against the patient's head. Preferably, the axis of the leadscrew or threaded rod may extend upward and downward relative to the patient when the patient is positioned for surgery, with a handle coupled to the threaded rod so as to manually drive the linkage from adjacent the patient's head.

In another aspect, the invention provides a method for restrainingly supporting a head of a patient. The head restraint method comprises receiving the head of the patient between a left sidewall and a right sidewall of a head pad body. The sidewalls extend from a central region and receive the head so that a back of the head engages the central region therebetween. The head pad body is deformed by articulating a linkage so as to move the left and right sidewalls inward, and so as to laterally compress the head therebetween sufficiently to inhibit movement of the head.

BRIEF DESCRIPTION OF THE DRAWINGS

FIG. 2 is a perspective view of a patient support for use in the laser eye surgery system of FIG. 1, in which the patient support has a headrest and neck rest which move vertically, and a compressive head pillow which restrains movement of the head during laser eye surgery or the like.

DETAILED DESCRIPTION OF THE INVENTION

The present invention generally provides improved devices, systems, and methods for supporting, positioning, and inhibiting inadvertent or undesired movements of patients. While the invention may find applications in a wide variety of settings, including for surgeries of the face, diagnostic measurements, and patient repositioning after injuries, the most immediate application for embodiments of the invention may be during refractive procedures such as laser eye surgery and the like. Advantageously, the structures and methods described herein may atraumatically and gently engage the patient's head, neck, and the like, optionally applying gentle and balanced forces to inhibit inadvertent motion of the patient, often without having to employ disconcerting or uncomfortable straps or the like. Advantageously, embodiments of these structures may facilitate both positioning and orienting a patient's head (particularly along the patient's medial-lateral plane) such as by moving the patient's head upward or downward, tilting the patient's face in a cranial or caudal direction, and other movements along the midline or bilateral plane of the patient. Positioning and inhibiting movement to the patient with embodiments of the invention can be performed quickly and easily, often from a position adjacent the patient's head while the patient's body is substantially horizontal (such as when the patient is lying on a substantially flat table, on a contoured or flat patient bed, on a reclined patient chair so that the patient is in a supine position, or the like). Access to the patient's eyes and significant portions (or all) of the patient's face may remain uninhibited.

Figure 1:
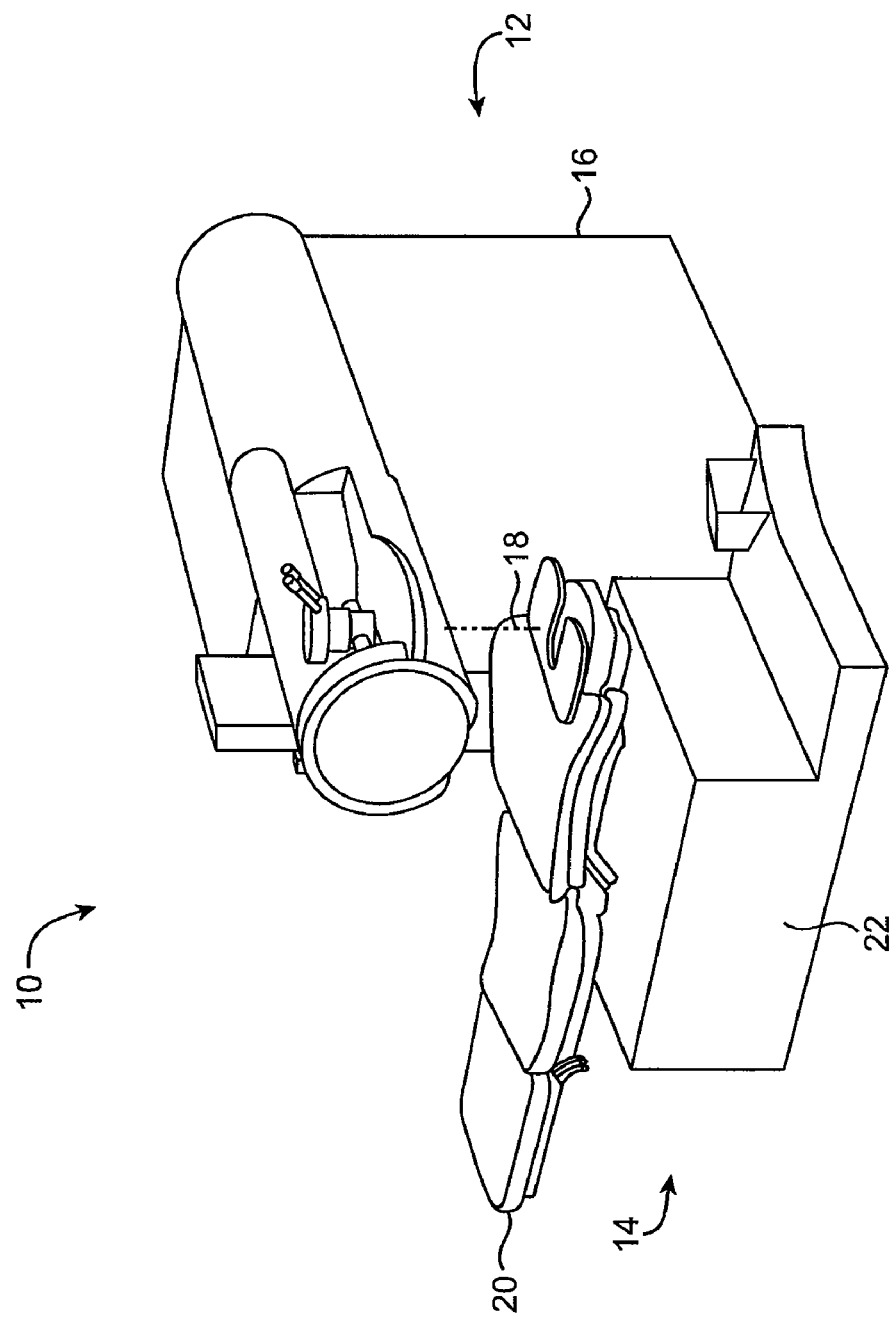
FIG. 1 is a perspective view schematically illustrating a laser eye surgery system having a patient support.

Referring now to FIG. 1, an exemplary laser eye surgery system 10 generally includes a laser system 12 and a patient support system 14. Laser system 12 includes a housing 16 that contains both a laser and system processor. The laser generates the laser beam 18 which is directed to a patient's eye for the processor under the direction of a system operator. Delivery optics used to direct the laser beam, the microscope mounted to the delivery optics, and the like may employ existing structures from commercially available laser systems, including at least some portions of the STAR S4 ACTIVE TRAK™ excimer laser system available from Advanced Medical Optics, Inc. of Santa Clara, Calif.

Figure 12:
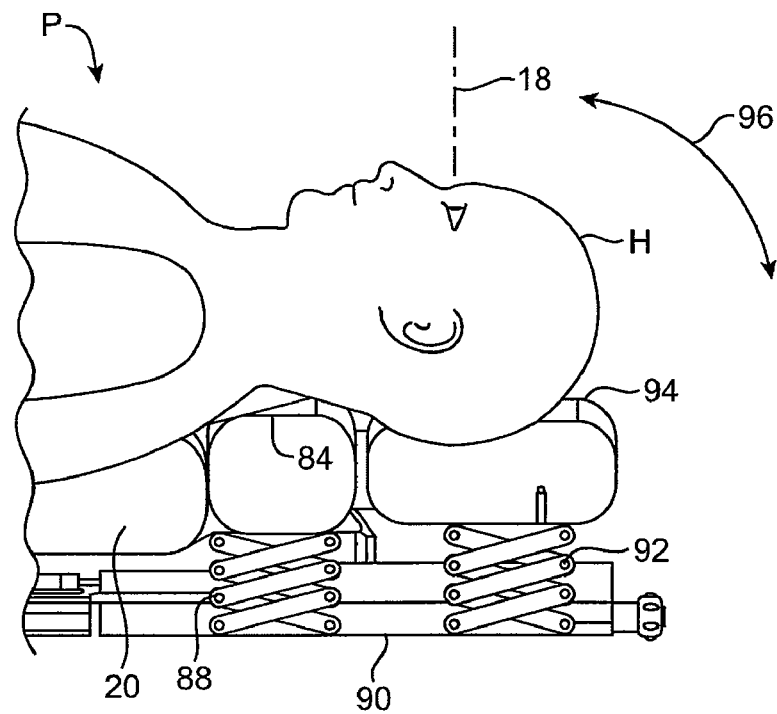
FIG. 12 is a side view schematically illustrating the independent scissor linkages for independently and linearly adjusting the height of the head pad and neck pad.
Figure 11:
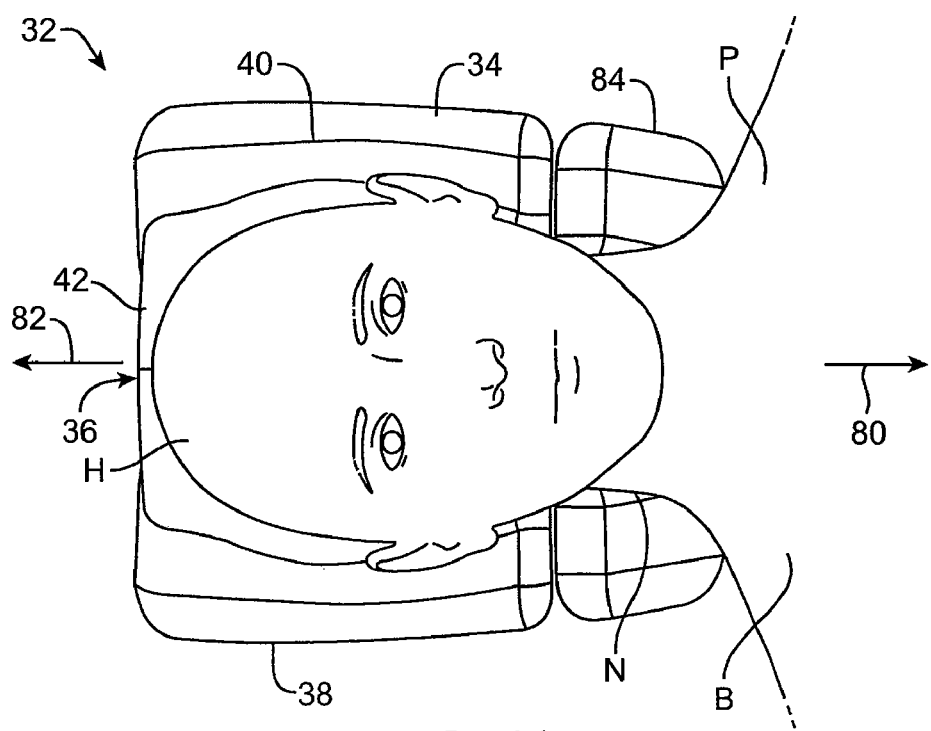
FIG. 11 is a view from above of a patient restrained by the head restraining pillow of FIG. 3A, and also shows a neck pad for orienting the patient's head along the patient's midline.
Figure 13:
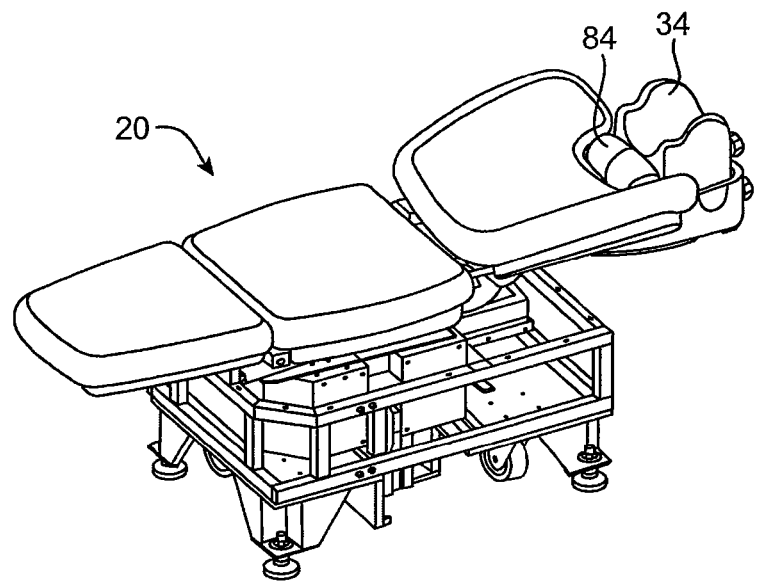
FIG. 13 is a perspective view from above of a patient support having linkages for independently varying a height of the patient's head and neck, in which the head pad comprises an articulating head restraint pillow.

The system operator interface for laser system 12 may include an input device 20 which can be used to help align laser beam 18 in relation to an eye of a patient P (see FIGS. 11 and 12). The microscope can be used to image a cornea of the eye, with the user interface optionally including a joy stick (or any of a variety of alternative input components such as a track ball, touch screens, or any of a wide variety of alternative pointing devices). Input to the processor of laser system 12 may also be provided a keypad, data transmission links such as an Ethernet, an intranet, the Internet, a modem, wireless devices, or the like.

In addition to (or in some cases, instead of) adjustments to the delivery optics directing laser beam 18, alignment between the patient and the laser treatment may be provided at least in part by the patient support system 14. Patient support system 14 generally includes a patient support 20 and a patient support movement mechanism 22. The patient support 20 may be contoured, helping to position the patient at a nominal location on the patient support such that the patient support defines nominal optical axes near the locations of the patient's left and right eyes. Movement mechanism 22 may allow the patient support 20 to move clear of the laser system 12 to facilitate loading and unloading of the patient onto the patient support, and may move the patient support quickly to a nominal left or right eye treatment position in which nominal optical axes defined by the patient support are aligned with laser beam 18. Fine adjustments of the patient support 20 position may then be effected using fine motion control of movement mechanism 22 so as to more accurately align the patient with the laser system, as more fully described in U.S. patent application Ser. No. 10/226,867, the full disclosure of which has previously been incorporated herein by reference.

The laser of laser system 12 will often comprise an excimer laser, ideally comprising an argon-fluoride laser producing pulses of laser light having a wavelength of approximately 193 nm. Each pulse of laser beam 18 preferably removes a microscopic layer of tissue, with the processor of laser system 12 scanning the pulses and/or profiling the pulses transmitted towards the patient's eye according to a pattern of pulses so as to resculpt the patient's cornea. Alternative laser or other electromagnetic radiation forms might also be used, particularly those well-suited for controllably ablating or reshaping corneal tissue without causing significant damage to adjacent and/or underlying tissues of the eye. Such laser systems may include solid state lasers, including frequency multiplied solid state lasers such as flash-lamp and diode pumped solid state lasers. Exemplary solid state lasers include UV solid state lasers having wavelengths of approximately 193-215 nm such as those described in U.S. Pat. Nos. 5,144,630 and 5,742,626.

In addition to lateral alignment between the patient and delivery optics of laser system 12, patient support 20 may also be used to help vertically position the patient (and more specifically, the eye of the patient) at a desired treatment location along the axis of laser beam 18. Such vertical adjustment of the patient or patient's eye can facilitate accurate ablation, imaging of the eye with the microscope of laser system 12, tracking movements of the eye so as to maintain alignment between laser beam 18 and the eye, and the like. In addition to providing vertical alignment, patient support 20 may also be used to orient the face and eye of the patient with the delivery optics and laser beam 18. While the patient will often be viewing a fixation target incorporated into the laser delivery optics of laser system 12 so as to help maintain the eye at the proper orientation relative to the therapeutic laser beam, having the patient's head at an appropriate orientation may facilitate access to the corneal tissue free from interference from the upper or lower eyelids. Proper orientation of the head may also make it easier for the patient to maintain viewing fixation on the fixation target.

Figure 1A:
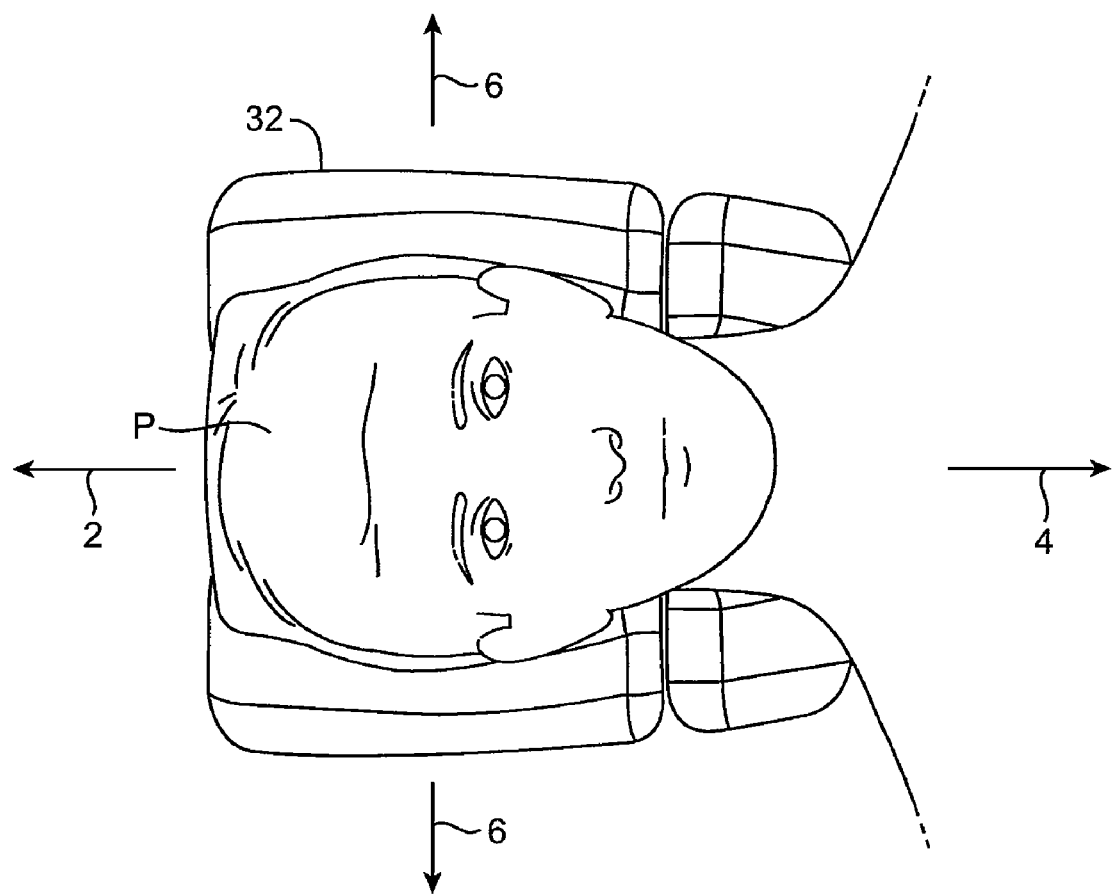
FIG. 1A is a top view of a head of a patient being supported by a compression head pillow, and shows various orientations relative to the patient.

Various orientations referenced to a patient P can be understood from FIG. 1A. Patient P generally has a medial-lateral plane, which extends along the boundary between the patient's right and left sides. The head of patient P will often be supported by pillow 32 during at least a portion of a procedure, and the pillow will often be contoured so as to comfortably receive the patient's head at desired orientation. A cranial orientation 2 relative to patient P generally references a direction toward or even beyond the top of the patient's head, and can also be used to describe an orientation relative to pillow 32. Similarly, a caudal orientation 4 relative to patient P or pillow 32 is inferior relative to the head of patient P (and/or pillow 32) toward or beyond the patient's abdomen or lower extremities. Lateral movement or rotation of patient P, a structure of pillow 32, or the like, generally references movement or rotation in the direction of lateral arrows 6.

Figure 2:
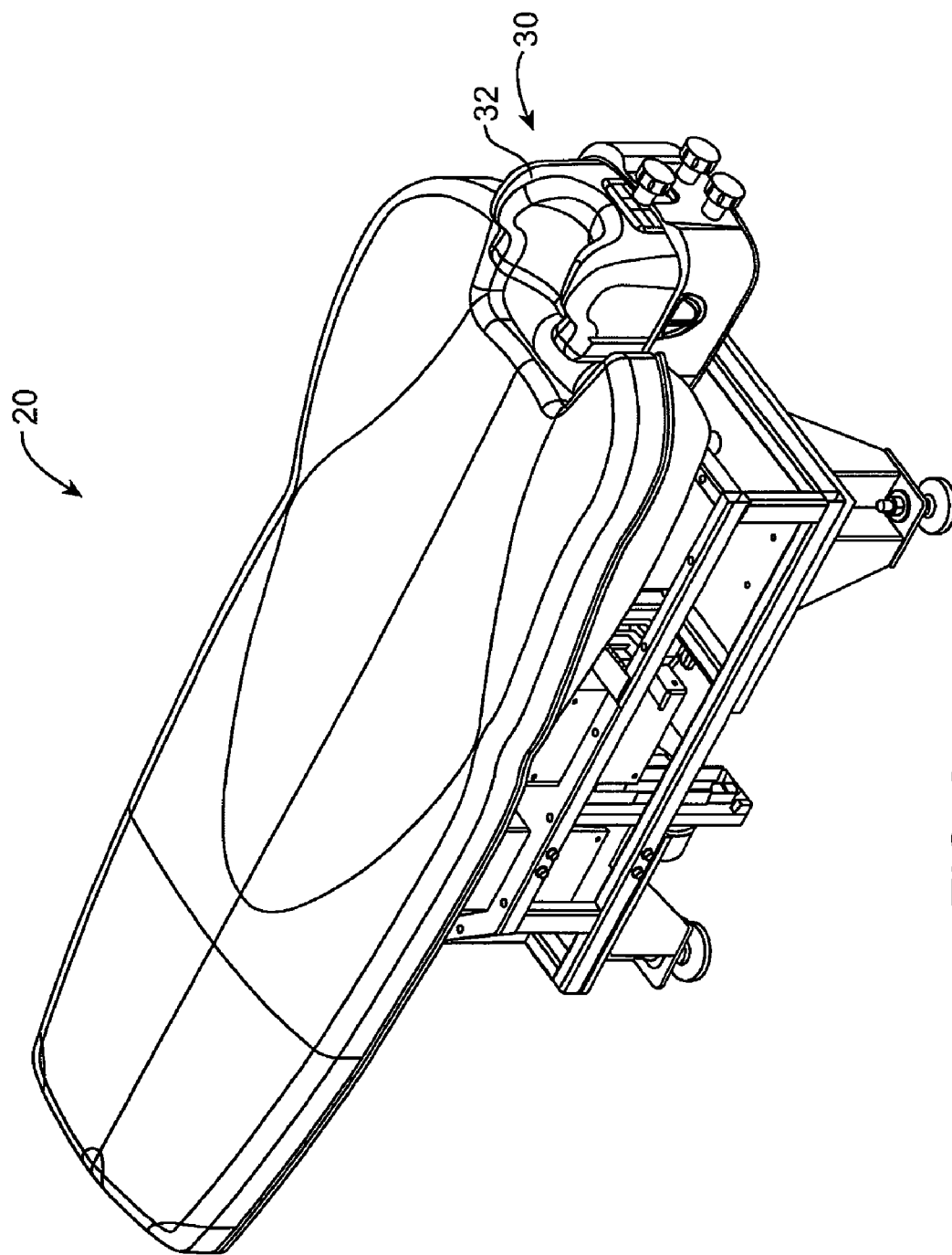

Referring now to FIG. 2, an exemplary patient support 20 can be seen in more detail. In some embodiments, the patient support may be articulated, optionally having a hinge or the like allowing the patient's legs or feet to be lowered independently of the torso. In many embodiments, a head support and/or restraint mechanism 30 may be provided. Exemplary head supports may take a variety of forms, optionally having head pad surfaces which are moderately contoured with a recess to receive the back of the patient's head, having variable stiffness surfaces, such as those provided by sealed head pad structures containing beads or the like which assume a more rigid configuration when a vacuum is applied, or having a highly contoured and articulated head pad structure that can apply gentle lateral compression to the sides of the head to inhibit movement of the head. In many embodiments, the position of the head pad 30 relative to the other portions of the patient support 20 may be moved, often by articulating one or more linkages.

Referring now to FIGS. 2, 3A, 3B, and 6, an exemplary head restraint mechanism 32 of head support 30 includes a head pad body in the form of an articulatable pillow 34 and an associated linkage 36. Pillow 34 includes a right sidewall 38, a left sidewall 40, and a central region 42 therebetween. The right and left sidewalls 38, 40 are generally configured to atraumatically engage at least a portion of a side of a patient's head when pillow 34 receives the head so that the back of the head engages and/or is adjacent to central portion 42. Ear recesses 44 in sidewalls 38, 40 provide clearance from (and inhibit injury to) the ears of the patient. In the exemplary embodiment, pillow 34 comprises a deformable material such as a molded urethane foam, a self-skinning urethane, a pressure and/or temperature sensitive visco-elastic foam material such as Tempur-Pedic foams sold commercially by Tempur-Pedic International Inc. of Kentucky, or the like.

Figure 3A:
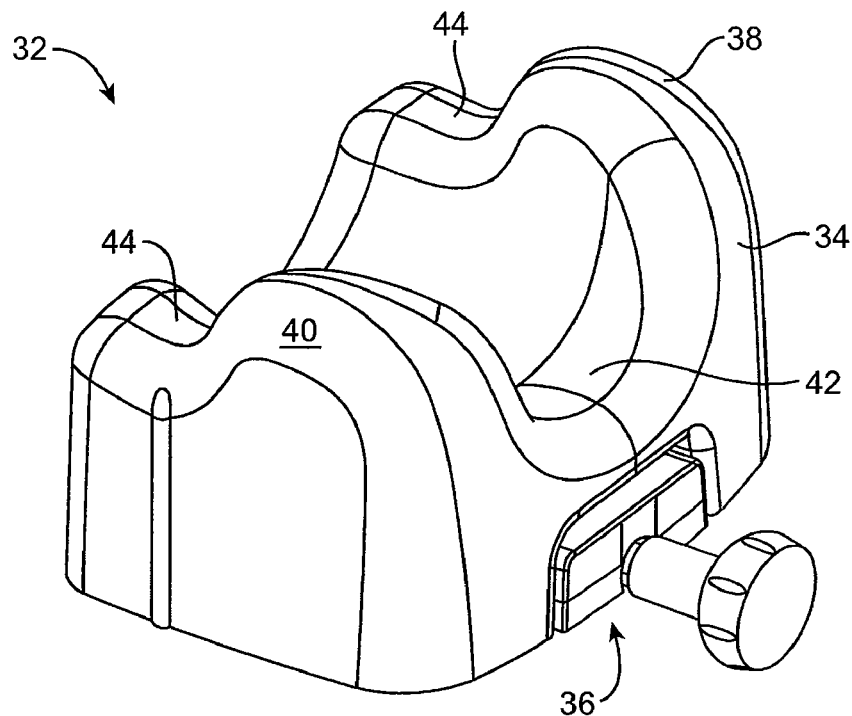
FIGS. 3A and 3B are perspective views from above and below, respectively, of a patient pillow and its associated actuation linkage for restraining movement of the patient's head.
Figure 3B:
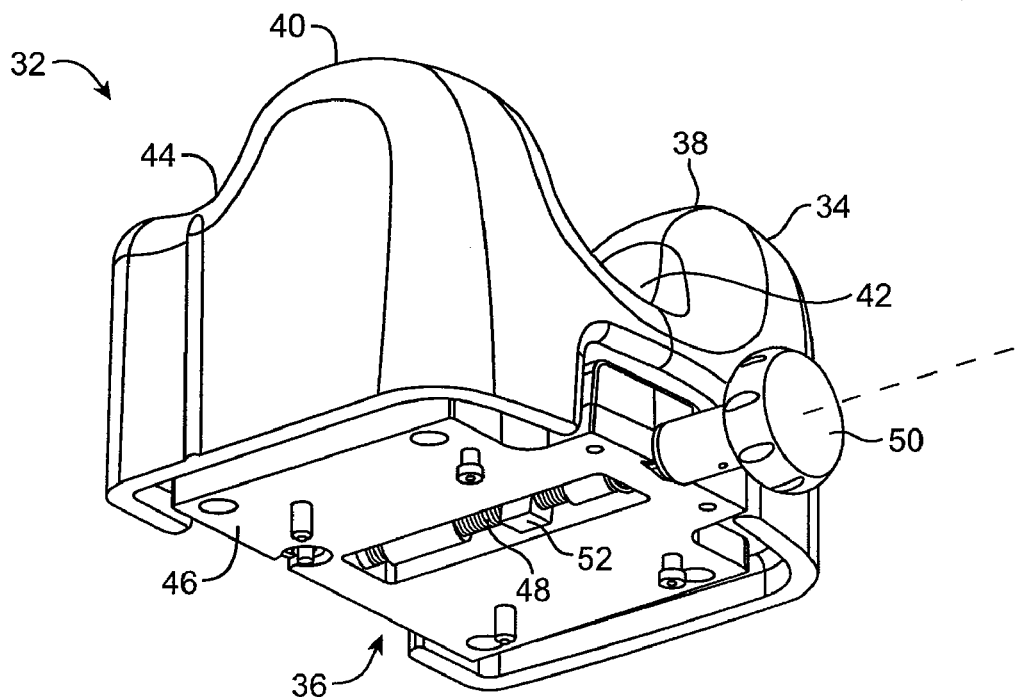

Portions of linkage 36 can be seen in FIG. 3B. In general, linkage 36 includes a base 46 to which a threaded rod or leadscrew 48 is rotatably coupled. A handle in the form of a rotatable knob 50 is coupled to leadscrew 48, with rotation of the knob generating movement of a leadscrew nut 52 (and hence of a cam follower 60 mounted thereon) along an axis of the leadscrew. A cam follower-and-channel linkage system produces vertical movement of a central portion of center region 42 in response to rotation of knob 50 using the axial movement of leadscrew nut 52.

Figure 4A:
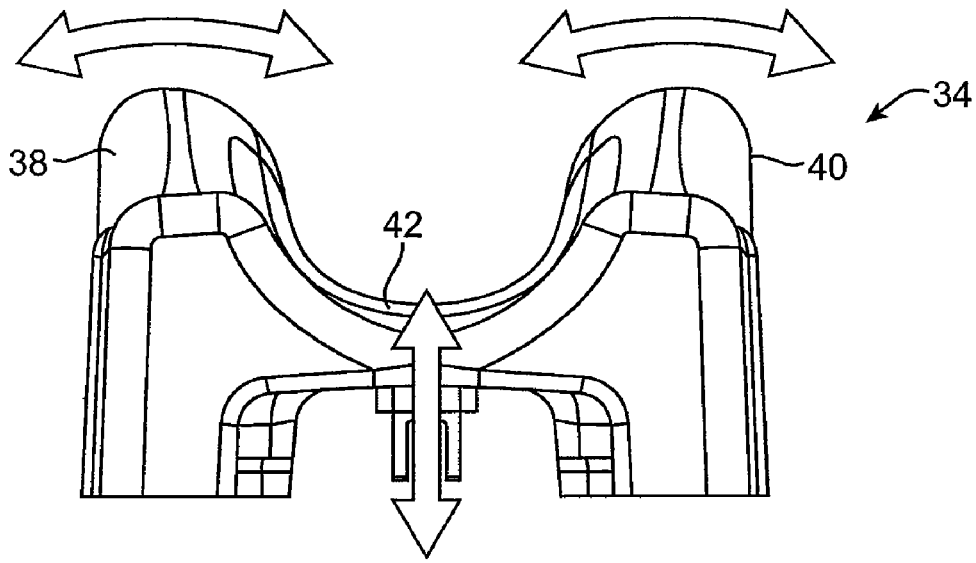
FIGS. 4A and 4B are an end view and a partial cutaway showing how vertical deflection of a central region of the patient pillow induces lateral deflection of the sidewalls.
Figure 4B:
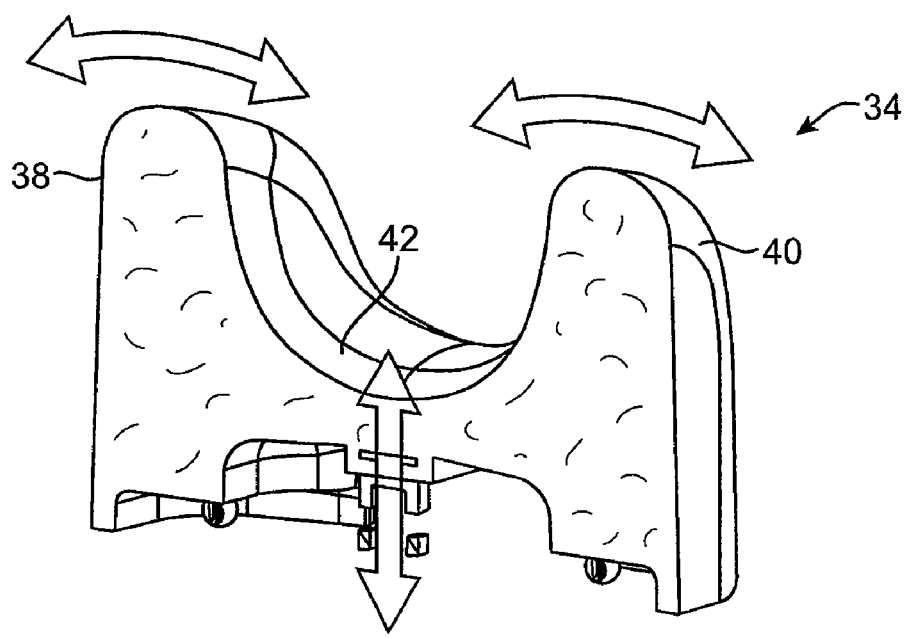

Referring now to FIGS. 4A and 4B, articulation of the pillow 34 as provided by the linkage 36 (see FIG. 3B) can be seen in more detail. As the linkage produces vertical movement along the midline of central portion 42, the base 46 (see FIG. 3B) of the linkage limits the vertical (particularly downward) motion of sidewalls 38, 40. As central portion 42 is drawn downward, the central portion acts as a translating living hinge, generating lateral deflection of the sidewalls 38, 40 in an inward direction. Alternative embodiments may have the sidewalls extending in an inward direction when pillow 34 is in a relaxed condition, with the linkage being used to force central portion 42 upward to allow the sidewalls to receive the head therebetween, with the pillow being articulated so as to return back towards its relaxed configuration.

Figure 5:
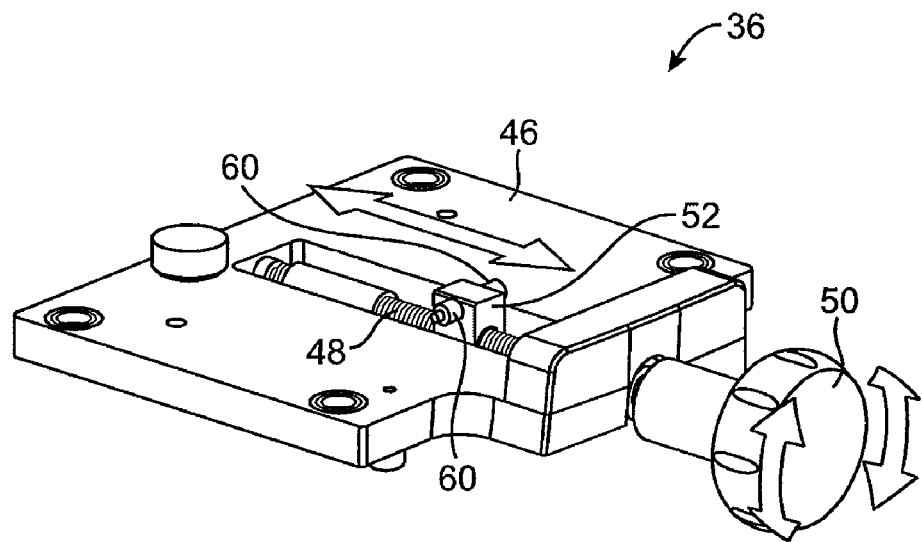
FIG. 5 is a perspective view of a portion of a linkage for articulating the patient pillow of FIG. 3A.
Figure 6:
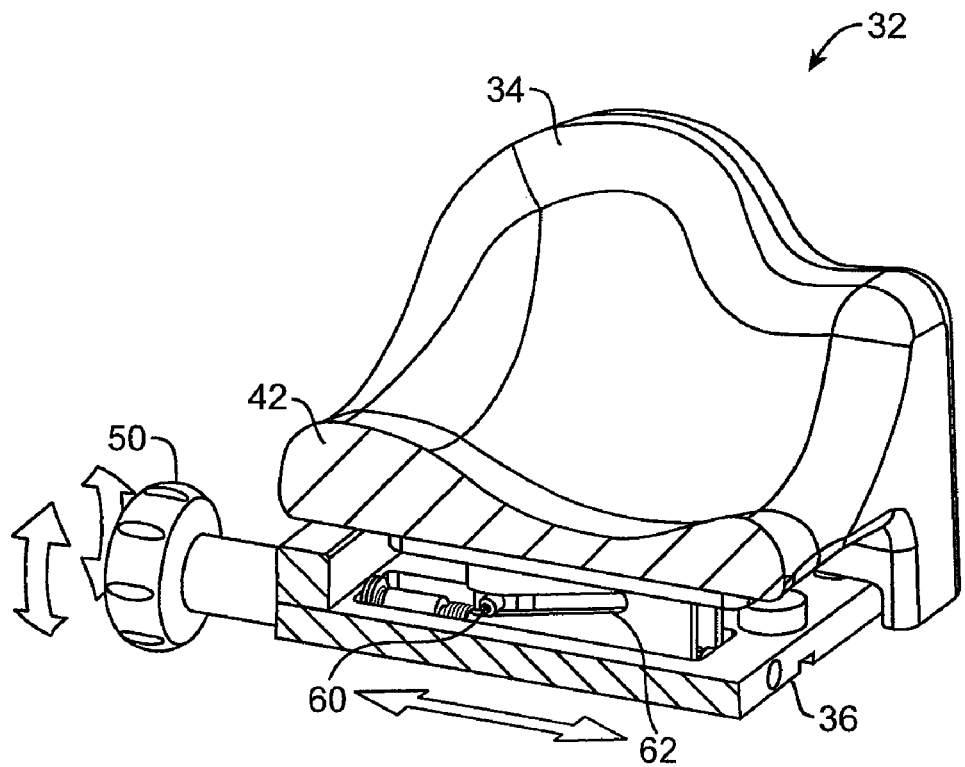
FIG. 6 is a partial cutaway view showing the articulation linkage of the head restraining patient pillow of FIG. 3A.

Referring now to FIGS. 5-8, the components of pillow articulation linkage 36 can be more fully understood. As seen in FIG. 5, rotation of knob 50 results in axial translation of leadscrew nut 52 via engagement with leadscrew 48, moving a cam follower 60 mounted to each side of the follower. The cam followers 60 are here in the form of a simple pin (with a roller bushing) which extends laterally from leadscrew nut 52, and which engage cam surfaces defined by a channel 62. Channel 62 is attached to the bottom of central portion 42 of the pillow. As rotatable knob 50 rotates, the axial movement of cam followers 60 within their associated channels 62 moves the central portion 42 of pillow 34 downward (towards a head compression configuration) or upward (as the pillow returns towards its nominal open configuration). The engagement between cams 60 and the surfaces of channel 62 are seen in FIG. 6.

Figure 7:
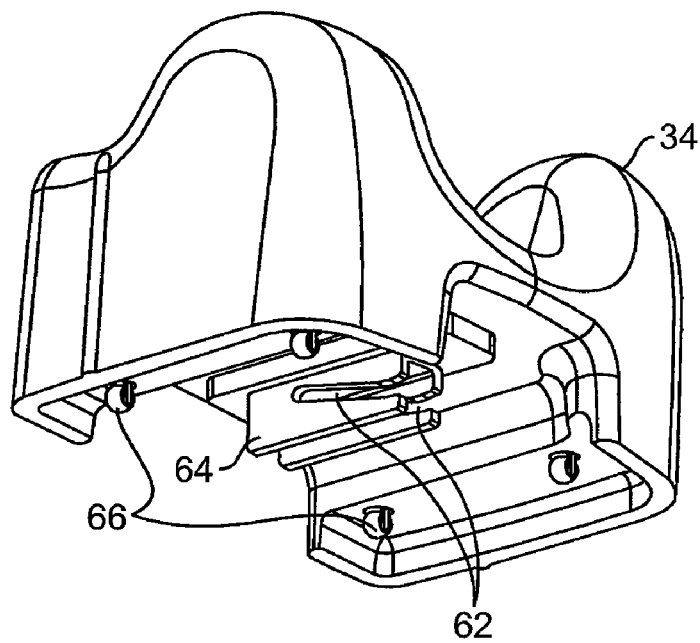
FIG. 7 is a view from below of the patient pillow of FIG. 3A, showing the cam of the articulation linkage attached thereto.
Figure 8:
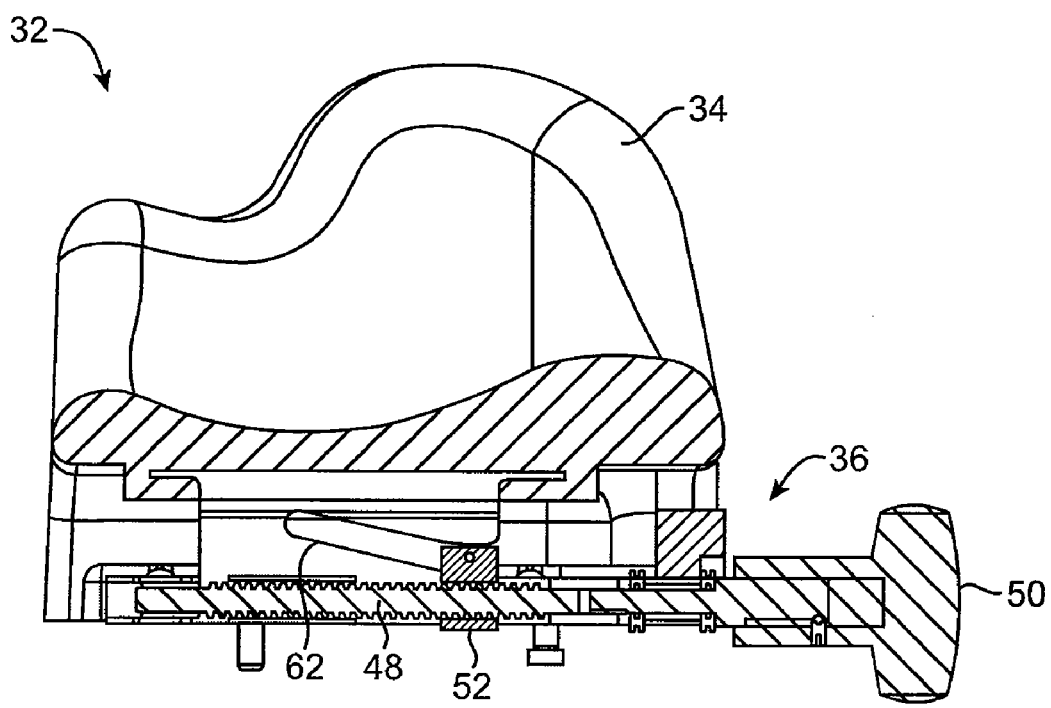
FIG. 8 is a cross sectional side view showing components of the articulation linkage and pillow assembly.
Figure 9:
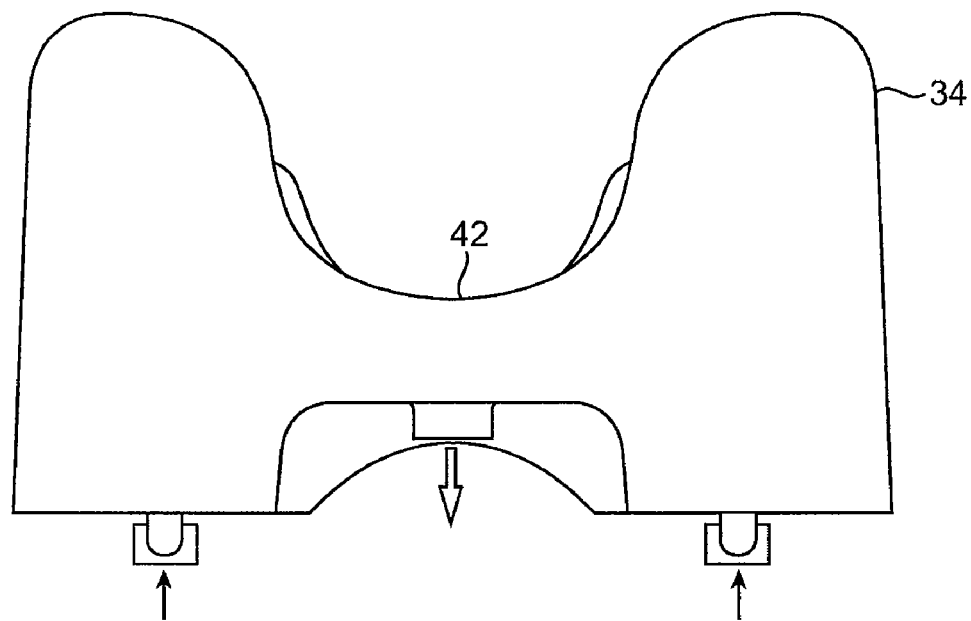
FIG. 9 is an end view showing forces applied by the articulation linkage on the body of the pillow.

The structure of a bracket 64 that extends downward from the central portion of pillow 34 so as to define the cam surfaces of channels 62 can be seen in more detail in FIG. 7. The exemplary bracket may comprise a polymer or metal, optionally comprising a plastic, aluminum, stainless steel, and/or the like, and may be attached to the structure of pillow 34 using adhesive bonding, ultrasonic welding, fasteners, heat bonding, insert molding, or the like. Base 46 and other components of the linkage 36 may also comprise metals or polymers, typically comprising plastic, aluminum, stainless steel, and/or the like. FIG. 7 also shows protruding bearing surfaces 66 that extend from a bottom of a lower surface of pillow 34 so as to engage base 46 of linkage 36 and inhibit downward movement of the sidewalls when the central portion of the pillow is drawn downward by the linkage. The cross sectional representation provided in FIG. 8 helps further show the interaction between pillow 34 and linkage 36, while the end view of pillow 34 in isolation of FIG. 9 helps show how a relatively thin cross section at the central portion 42 allows that structure to act as a vertically translating living hinge when the cam-and-cam follower structure pulls the central portion downward and the base 46 provides upward reactive forces at surfaces 66.

Figure 10:
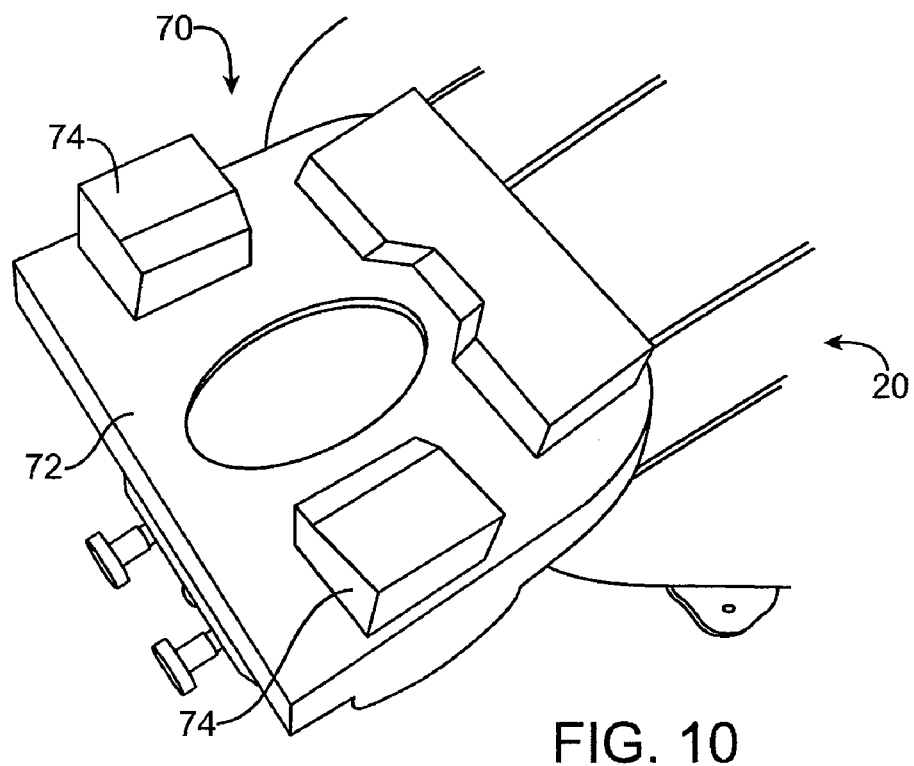
FIG. 10 is a perspective view from above of an alternative head restraining pillow.

An alternative embodiment of an articulated pillow 70 is illustrated in FIG. 10. In this embodiment, articulated pillow 70 includes a base portion 72 with a central portion having a cutout for receiving the back of the head and sidewalls 74. The material of the base portion 72 may differ from the sidewall 74, and a neck pad is here affixed to the base portion independently of the sidewalls. Such a pillow may be actuated differently, with the sidewalls compressing laterally against the patient's head as he/she lays down. A variety of alternative pillow configurations may also be provided.

FIG. 11 is a view from above of a patient P with a head H on head support 32. Patient P generally defines a caudal orientation 80 and a cranial orientation 82 when disposed on head support 32 and patient support 20. The head support 32 is generally symmetric about a medial-lateral plane of the patient P. The medial-lateral plane of patient P is generally the plane of symmetry between the patient's left and right sides.

Also seen in FIG. 11 is a neck pad 84 which engages the patient adjacent a neck N between head H and a body B of the patient P. Neck pad 84 will generally be disposed in a caudal direction from pillow 34, and may optionally engage the patient along the upper portion of the neck and/or lower portion of the back of the head, at the base of the neck, or the like. In many embodiments, neck pad 84 may be supported by a linkage which allows linear vertical movement of the neck pad. Pillow 34 which engages the head H of patient P may also be supported by a linkage which allows linear vertical movement of the head engaging pillow surface or head pad, with the two linkages optionally allowing independent vertical movement of these two different support surfaces.

As can be understood with reference to FIG. 12, a first scissor linkage 88 supports neck pad 84 relative to a head support base 90, while a second scissor linkage 92 supports a head pad 94 relative to base 90. As mentioned above, head pad 94 may optionally comprise a contoured head pad having a receptacle for receiving the back of head H, a restraining head pad body such as articulated pillow 34 (see FIG. 11), a vacuum pillow, a flat pillow, or the like. The top of the head pad linkage may comprise or support an articulating head restraint linkage base 46, as can be understood with reference to FIGS. 2 and 3B. Articulation of head pad linkage 92 generally allows a height of head H to be varied along a vertical axis and/or along the axis of treatment laser 18. Articulation of scissor linkage 88 supporting neck pad 84 allows an angle of head H to be varied along the patient's medial-lateral plane, as schematically illustrated by arrow 96.

Figure 14:
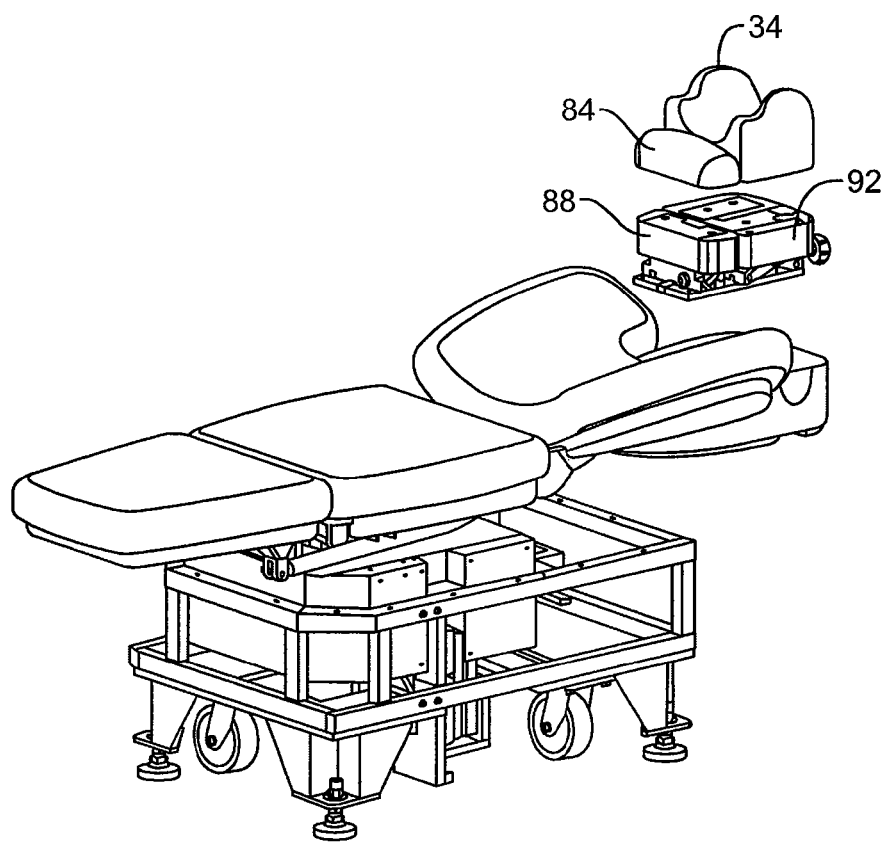
FIG. 14 is an exploded view of the patient support of FIG. 13, showing the head and neck height adjustment linkages.
Figure 15:
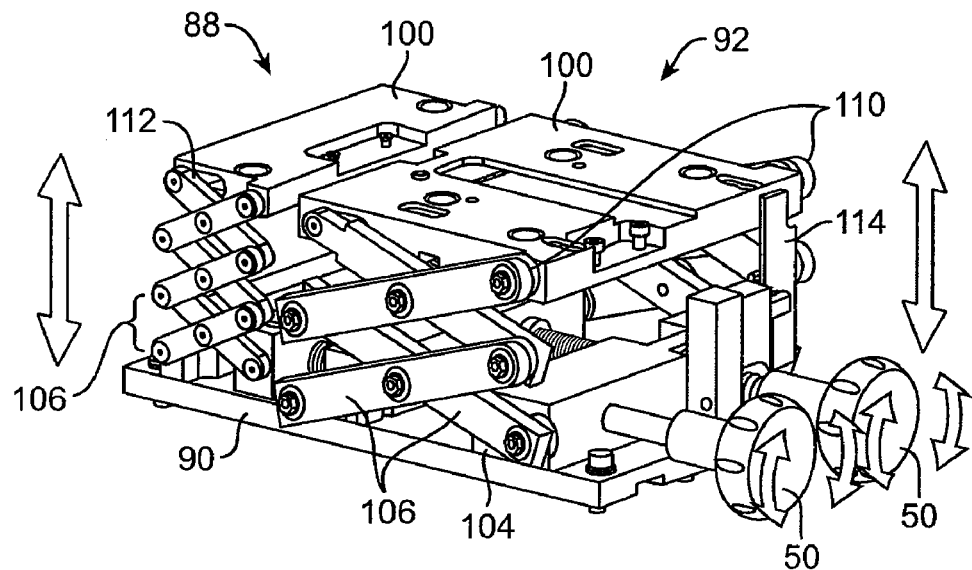
FIG. 15 is a perspective view of exemplary scissor linkages for adjusting the height of the patient's head and neck in the patient support of FIG. 13.
Figure 16:
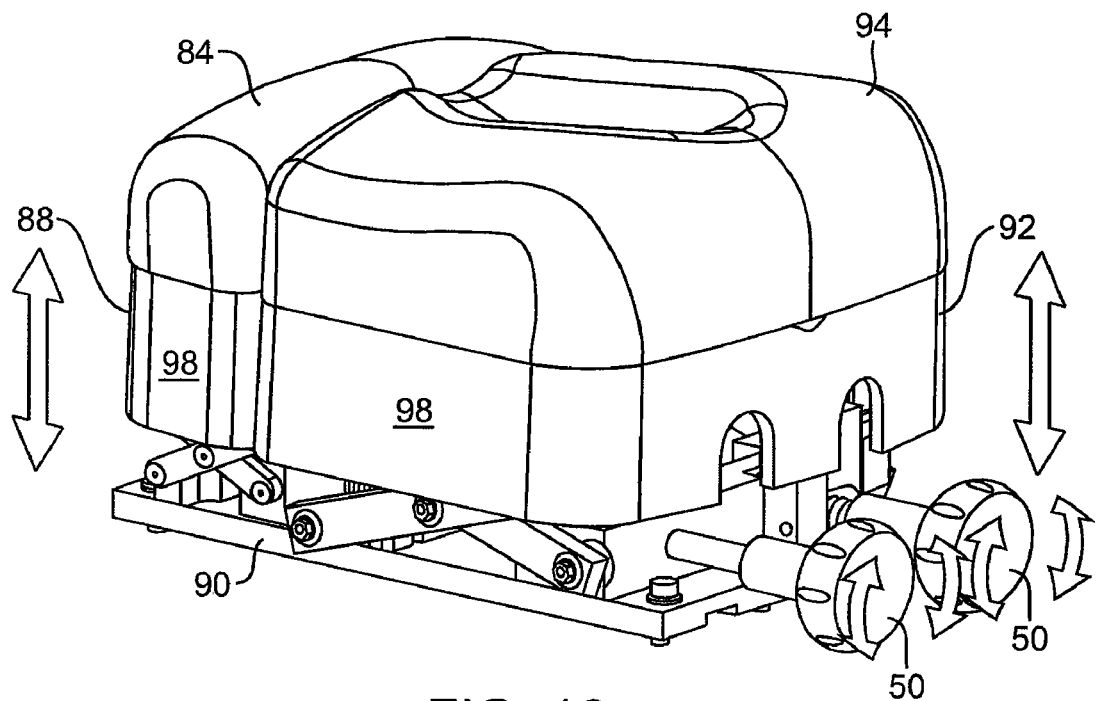
FIG. 16 is a perspective view of an adjustable patient support mechanism similar to that used in FIG. 13, with the head pad here comprising a non-head restraining contoured pillow.

The arrangement of neck pad 84 and an exemplary head pad defined by the surface of articulatable pillow 34 can be understood with reference to FIGS. 14 and 15. The linkages 88, 92 supporting the neck pad 84 and pillow 34 are independently adjustable by a system operator disposed adjacent the patient's head. A shield 98 may at least partially surround each linkage below its associated pad to prevent fingers of the system operator or other medical personnel from being pinched between the links as the linkages move, as illustrated in FIGS. 15 and 16.

The structure of linkages 88 and 92 which effect linear movement of the neck pad and head pad may be understood with reference to FIGS. 15, 16, 17A, and 17B. Although some embodiments may employ linkages which are actuated using electrical power, hydraulic power, or the like, the exemplary embodiments are manually actuated by movement of a handle, and more specifically by rotation of a rotatable knob 50. Each linkage moves its associated pad by about one inch or more, in many embodiments providing a vertical motion of about two inches or more. Linkages 88, 92 preferably inhibit rotation of the pad relative to base 90. While a number of different specific linkage structures might be employed to provide this linear motion, including rack and pinion linkages, cam and follower linkages, and the like, the exemplary linkages comprise scissor linkages so as to provide linear motion of a linkage top 100 associated with each linkage 88, 92.

Figure 17A:
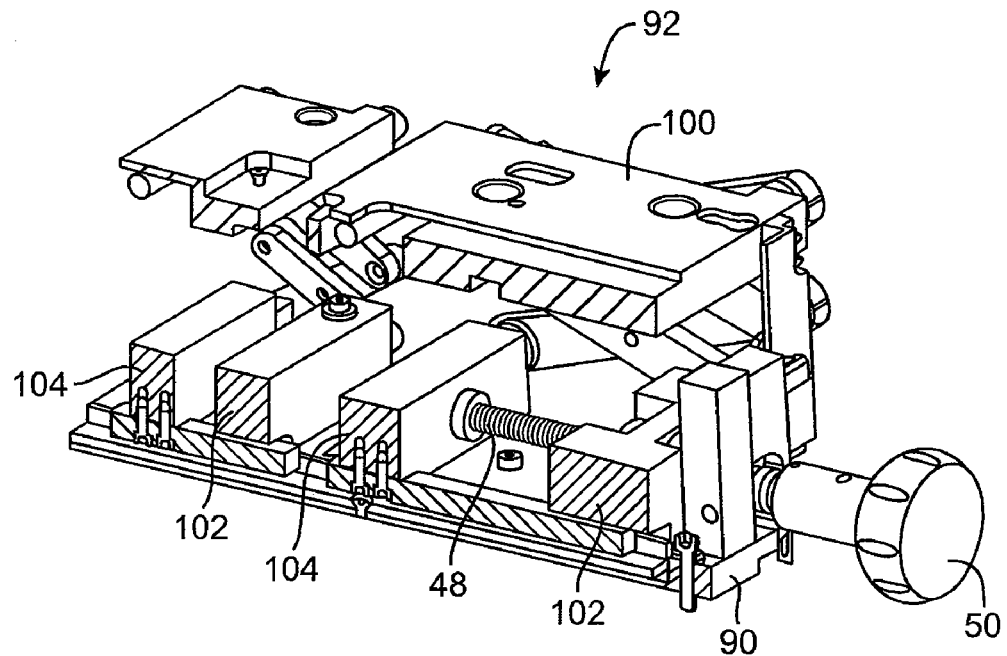
FIGS. 17A and 17B are perspective cutaway views showing internal components of the scissor linkages used for varying a height of the head pad, and neck pad, respectively in the patient support of FIG. 13.

Referring now to FIG. 17A, rotation of a handle 50 of head pad linkage 92 causes rotation of a threaded rod 48 to which the handle is coupled. A fixed block 104 is coupled to a moving block 102 by leadscrew 48, with the fixed block having a bearing allowing rotation of the threaded rod and the moving block having a threaded nut supported by a linear slide structure. As the nut of moving block 102 draws the moving block axially along the axis of leadscrew 48, it pushes the ends of a scissor link pair 106 towards each other (see FIG. 15). Each linkage of the scissor link pair 106 is coupled together at a middle of the link, and scissor link pairs may be stacked as illustrated on FIG. 15 along either side of head pad linkage 92 (and similarly along the sides of neck pad linkage 88).

So as to keep linkage top 100 parallel to base 90, one of the top scissor links is pivotally coupled to the linkage top 100 at a pivotal joint 110. The other top link of the scissor link pair slidingly engages the linkage top 100 at a sliding joint 112. This allows the top ends of the scissor link pair to move closer together, corresponding to the movement of the bottom ends of the bottom scissor link pair during axial motion of moving block 104.

Figure 17B:
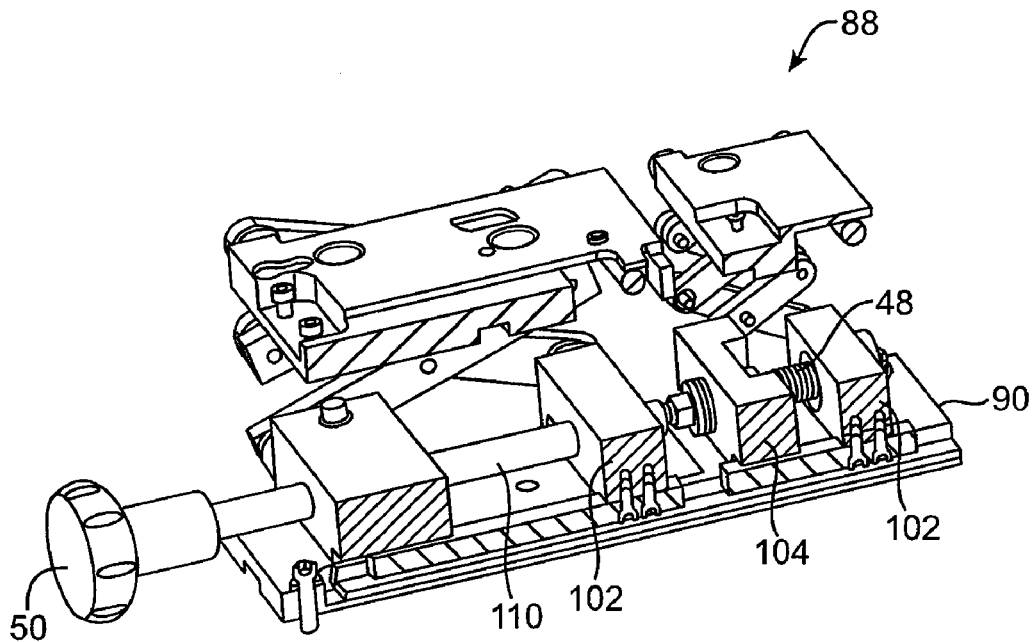

As can be understood by a comparison of FIG. 17B with FIG. 17A, and further in view of FIG. 15, neck pad linkage 88 includes many components similar to those of head pad linkage 92, with a shaft 110 extending between knob 50 and the leadscrew 48 of the neck pad linkage. Shaft 110 and the moving block 102 of head pad linkage 92 may accommodate both axial rotation of the shaft and axial movement of the head pad linkage moving block, thereby allowing the linkages to move independently while still providing access to both knobs from adjacent the patient's head.

A variety of refinements may be provided to the head positioning and/or restraint mechanisms described herein. For example, at least one of the knobs 50 may have a locking mechanism 114 which inhibits rotation of the associated threaded rod when the knob is moved axially to a locked position. Suitable locking mechanisms may make use of axial spines or key ways within knob 50 that only engage when the knob is in an appropriate axial position, or the like.

While the exemplary embodiments have been described in some detail for clarity of understanding and by way of example, a variety of additional modifications, adaptations, and changes may be clear to those of skill in the art. Hence, the scope of the present invention is limited solely by the appended claims.

What is claimed is:

1. A head restraint mechanism for restrainingly supporting a head of a patient, the head restraint mechanism comprising:
   a head pad body having a left sidewall and a right sidewall extending from a central region therebetween, the head pad configured to receive the head of the patient between the left and right sidewalls when the back of the head receives the central region; and
   a linkage coupled to the head pad body, actuation of the linkage articulating the head pad body so as to move the left and right sidewalls inward, and so as to laterally compress the head therebetween sufficiently to inhibit movement of the head,
   wherein the linkage comprises a cam follower movable along an associated cam surface so as to move the central portion vertically, and
   wherein the linkage comprises a leadscrew having an axis and rotatably coupled to a base, wherein the cam surface is affixed to the central portion, and wherein the cam follower moves axially with rotation of the leadscrew so that engagement between the cam surface and the cam follower moves the central portion vertically while the base inhibits vertical movement of the sidewalls.

2. The head restraint mechanism of claim 1, wherein the head pad body comprises a deformable foam.

3. The head restraint mechanism of claim 2, wherein the head pad body comprises a urethane foam or a pressure sensitive visco-elastic foam.

4. The head restraint mechanism of claim 1, wherein the sidewalls have ear recesses.

5. The head restraint mechanism of claim 1, wherein the axis of the leadscrew extends in a caudal cranial orientation relative to the patient when the patient is positioned for surgery inwardly of the left and right sidewalls of the head pad body and defines a first direction and a second direction, and wherein a drive handie is coupled to the leadscrew threaded rod toward the first direction from cranially of the cam so as to manually drive the linkage.

6. The head restraint mechanism of claim 1, further comprising a base and a linkage varying a height of the head pad body relative to the base.

7. A method for restrainingly supporting a head of a patient, the head restraint method comprising:

receiving the head of the patient between a left sidewall and a right sidewall of a head pad body, the sidewalls extending from a central region and receiving the head so that a back of the head is received by the central region;

deforming the head pad body by articulating a linkage so as to move the left and right sidewalls inward and laterally compress the head therebetween sufficiently to inhibit movement of the head;

wherein deforming the head pad body by articulating a linkage comprises drawing the central region downward to deflect the sidewalls;

wherein articulating the linkage comprises rotating a leadscrew, wherein the leadscrew induces cam-and-follower movement of the linkage so as to draw the central region downward to deflect the sidewalls.

* * * * *